United States Patent
Yamamoto et al.

(10) Patent No.: US 7,144,357 B2
(45) Date of Patent: Dec. 5, 2006

(54) METHOD AND APPARATUS FOR FOLDING CONTINUOUSLY FED WEB IN TWO

(75) Inventors: Hiroki Yamamoto, Mitoyo-gun (JP); Hirofumi Onishi, Mitoyo-gun (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/101,392

(22) Filed: Apr. 8, 2005

(65) Prior Publication Data
US 2005/0181921 A1  Aug. 18, 2005

Related U.S. Application Data

(62) Division of application No. 10/901,345, filed on Jul. 29, 2004, now Pat. No. 6,926,654.

(30) Foreign Application Priority Data
Jul. 31, 2003 (JP) .............................. 2003-204426

(51) Int. Cl.
*B31B 49/00* (2006.01)
(52) U.S. Cl. .................... 493/34; 493/19; 493/23; 493/254
(58) Field of Classification Search .............. 493/19, 493/34, 13, 23, 81, 254, 425, 434, 442
See application file for complete search history.

(56) References Cited

U.S. PATENT DOCUMENTS

| 2,265,075 | A | * | 12/1941 | Knuetter | 493/197 |
| 3,897,943 | A | * | 8/1975 | Head et al. | 493/434 |
| 4,012,268 | A | * | 3/1977 | Johnsen | 156/200 |
| 4,041,849 | A | * | 8/1977 | Tsukasaki | 493/436 |
| 4,650,530 | A | | 3/1987 | Mahoney et al. | |
| 5,217,739 | A | * | 6/1993 | Stein et al. | 426/496 |
| 6,562,171 | B1 | * | 5/2003 | Archie et al. | 156/204 |
| 2002/0174930 | A1 | | 11/2002 | Umebayashi et al. | |

FOREIGN PATENT DOCUMENTS

| JP | 1977-29339 | 3/1977 |
| JP | 2003-38566 | 2/2003 |

* cited by examiner

*Primary Examiner*—Sameh H. Tawfik
(74) *Attorney, Agent, or Firm*—Lowe Hauptman & Berner LLP

(57) ABSTRACT

Here is disclosed a method and apparatus for folding a continuously fed in two. The web is folded along guide means defining a folding guide line with a fold angle gradually reduced. In the course of gradually reducing the fold angle, a plurality of guide rolls through are pressed against transversely opposite side edge portions of the web. Immediately before the stage on which the web is completely folded in two, there are provided detector means adapted to detect actual positions of the respective side edge portions and swing rolls located upstream of these detector means adapted to change a crossing angle of the web with respect to a machine direction. Actuators interposed between the detector means and the swing guide rolls cause the swing guide rolls to swing and thereby to move the side edge portions toward predetermined positions.

1 Claim, 5 Drawing Sheets

METHOD AND APPARATUS FOR FOLDING CONTINUOUSLY FED WEB IN TWO

RELATED APPLICATIONS

The present application is a divisional application of U.S. patent application Ser. No. 10/901,345, filed Jul. 29, 2004, now U.S. Pat. No. 6,926,654.

BACKGROUND OF THE INVENTION

This invention relates to a method and apparatus for folding a continuously fed web in two. Such a method and apparatus are adapted to be used for continuous production of disposable pull-on wearing articles such as disposable pull-on diapers.

Japanese Unexamined Patent Application Publication No. 1977-29339 (Citation 1) discloses the invention relating to "Method and apparatus for folding and cutting continuous web". The invention disclosed in this document allows a continuously fed web comprising a series of diapers successively connected one to another and including elastic strands stretched in parallel to a direction in which the web travels to be folded along a longitudinal direction from its transversely flattened state so that the web may present a C-shaped cross-section. For such folding, a board folder of well known art is used.

U.S. Pat. No. 4,650,530 (Citation 2) discloses the invention relating to a method and apparatus for folding, bonding and cutting a continuously fed web. According to the disclosure of this document, a projection radially extending from a periphery of a rotary disc come in contact with a transversely middle region of the web running in a machine direction and serve as point of support for the web which is, in turn, folded in two lying on both sides of the rotary disc, respectively. The apparatus disclosed in this document allows the pants-type wearing article to be continuously manufactured.

Japanese Unexamined Patent Application Publication No. 2003-38566 (Citation 3) discloses a method and apparatus for making disposable wearing articles. Such a method and apparatus use a folder adapted to fold a web in two so that transversely opposite side edges of the web may be placed upon each other, an adjuster adapted to position-adjust the web, a detector adapted to detect an actual line along which the web is being folded, and a controller adapted to control the adjuster on the basis of information supplied from the detector. The adjuster includes a web guider which includes, in turn, guide rolls extending across the web before folded in two. The guide rolls are in contact with the web in the vicinity of its transversely opposite side edges and controlled by the controller to swing so that a cross angle of the web with respect to a direction in which the web runs may be changed. Depending on the cross angle, the guide rolls adjust a tension in the web's running direction exerted on the web in the vicinity of its transversely opposite side edges so that the web may run along a predetermined path.

With the method and apparatus disclosed in Citation 1, the web is folded along edges of the board folder opposed to each other when the web is folded in the transverse direction so as to present the C-shaped cross-section. However, there is provided none of particular means serving to align the web and the board folder with each other and therefore the web can not present the expected C-shaped cross-section if the transversely middle region of the web is out of alignment with the transversely middle region of the board folder.

The method and apparatus disclosed in Citation 2 also have none of particular means serving to align the projection of the disc with the transversely middle region of the web. If the web is out of alignment with the disc in the transverse direction, the pants-type wearing article obtained will have respective ends of the front and rear waist regions being out of mutual alignment in a direction of the article's height.

The method and apparatus disclosed in Citation 3 use the guide rolls extending across the web to guide the web so that, as one of the side edges of the web is position-changed, the other side edge also is correspondingly position-changed. While these method and apparatus are effective so far as these method and apparatus are used for a non-stretchable web, it is difficult to expect the same effect when these method and apparatus are used for elastically or inelastically stretchable web. This is because the other side edge of the web is not necessarily position-changed in accurate correspondence with the position-change of the one side edge of the web. Furthermore, while it is possible for these method and apparatus to position-change the side edges of the web before the web is folded in two, it is impossible to position-change the side edges of the web once the web has begun to be folded. In addition, if a distance from the point at which the web has begun to be folded to the point at which the web is completely folded is relatively long, a distance of a downstream region from the guide rolls will be correspondingly long. Consequently, the function of the guide rolls to position-adjustment of the web is hardly effective upon the web which have already been folded. In other words, it is difficult for these guide rolls to maintain the exact relative positions of the transversely opposite side edges of the web which has been folded in two.

SUMMARY OF THE INVENTION

It is an object of this invention to improve the conventional technique for folding the web which continuously run in the machine direction in the transverse direction so that the transversely opposite side edges of the web can be easily controlled to maintain the expected positions.

The object set forth above is achieved by a method and apparatus according to this invention.

This invention on one aspect relates to a method for continuously folding a web continuously fed in a machine direction in two along a folding guide line extending in parallel to the machine direction in a cross direction orthogonal to the machine direction.

The method according to this invention comprising the stages of: continuously feeding the web in said machine direction along a guide means defining the folding guide line so that the web may be folded by a plurality of guide rolls arranged intermittently in the machine direction, the guide rolls being rotatable in the machine direction in contact with transversely opposite side edge portions of the web and having rotary shafts crossing the side edge portions of the web at an angle of 90° or less opening in a direction in which the web is fed, so that a fold angle of the web in the cross direction may be gradually reduced; downstream of the guide rolls and immediately before a stage of completely folding the web, providing detector means adapted to detect positions of the side edge portions in the cross direction, swing guide rolls located upstream of the detector means so as to be held in contact with respective the side edge portions and thereby to change the crossing angle of the web with respect to the machine direction and actuators interposed between these detector means and the swing guide rolls; and energizing the actuators on the basis of differences between data supplied from the detector means representing actual positions of the side edge portions and data representing expected positions of the side edge portions so that the swing guide rolls may swing and thereby move the side edge portions toward the expected positions.

According to one preferred embodiment of the invention relating to the method, the web comprises at least one of an elastically or inelastically stretchable nonwoven fabric, woven fabric and plastic film. According to another preferred embodiment of the invention relating to the method, the web is destined to define a front waist region, a rear waist region and a crotch region of a disposable pull-on wearing article.

This invention on another aspect relates to an apparatus for continuously folding a web continuously fed in a machine direction in two along a folding guide line extending in parallel to the machine direction in a cross direction orthogonal to the machine direction.

The apparatus according to this invention comprises: a first means located upstream in the machine direction and adapted to feed the web unfolded in the transverse direction; a second means located downstream in the machine direction and adapted to convey the web having been folded in two; a guide means interposed between the first means and the second means and adapted to be pressed against the web along the folding guide line to fold the web in two; a plurality of guide rolls arranged intermittently in the machine direction and adapted to be held in contact with the side edge portions, each of the guide rolls having a rotary shaft crossing the side edge portions of the web at an angle of 90° or less opening in the transverse direction of the web; swing guide rolls located downstream of the guide rolls and adapted to be held in contact with the side edge portions of the web and, in addition, to swing so that a crossing angle thereof with respect to the side edge portions of the web may be changed; detector means located downstream of the swing guide rolls and adapted to detect positions of the side edge portions in the cross direction; and actuators causing the swing guide rolls to swing on the basis of differences between data supplied from the detector means representing actual positions of the side edge portions and data representing expected positions of the side edge portions to move the side edge portions toward the expected positions.

DETAILED DESCRIPTION OF THE PREFERRED EMBODIMENTS

Details of a method and apparatus for folding a continuously fed web in two will be more fully understood from the description given hereunder with reference to the accompanying drawings.

Figure 1:
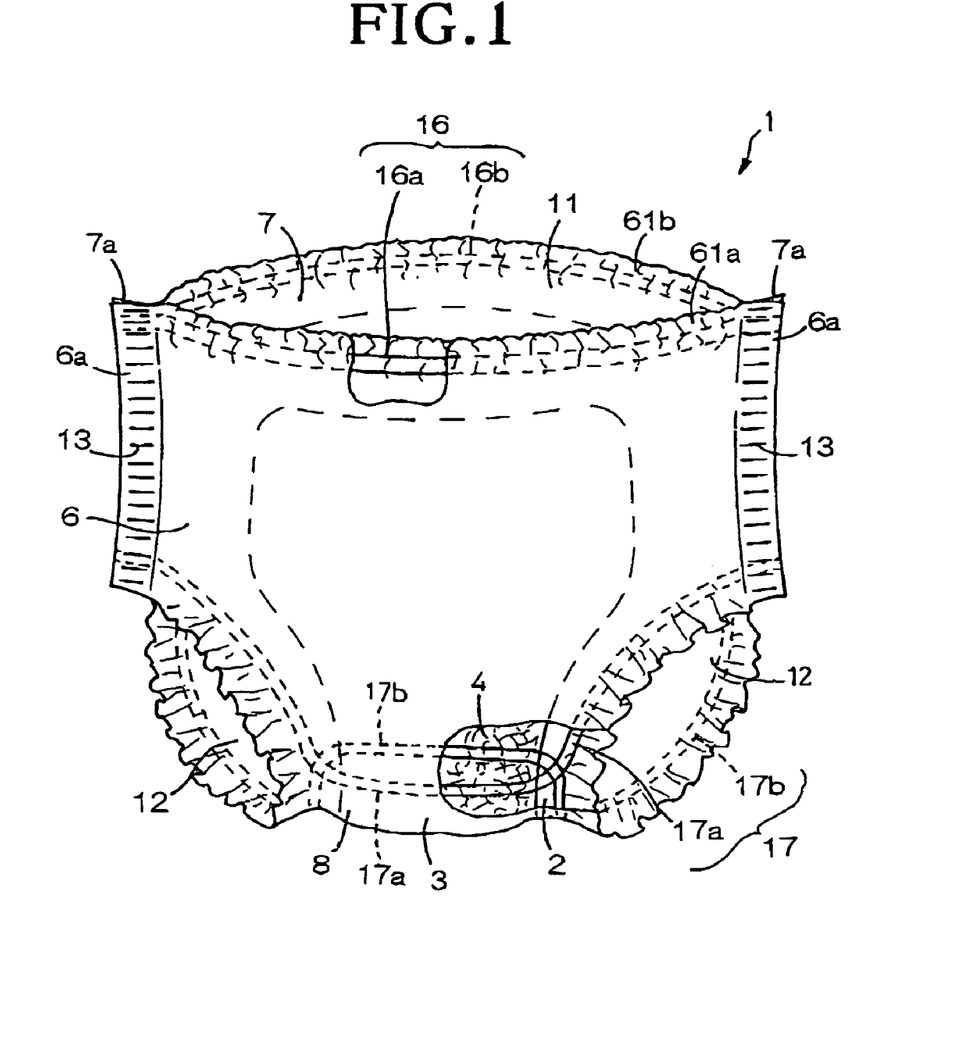
FIG. 1 is a perspective view showing a disposable pull-on diaper.

FIG. 1 is a partially cutaway perspective view showing a disposable pull-on diaper 1 obtained by a method and apparatus according to this invention. The diaper 1 is formed from a liquid-pervious topsheet 2 facing the wearer's skin, a liquid-impervious backsheet 3 facing away from the wearer's skin and a liquid-absorbent core 4 interposed between these two sheets 2,3 and has a front waist region 6, a rear waist region 7, a crotch region 8, a waist-hole 11 and a pair of leg-holes 12. The front waist region 6 and the rear waist region 7 are integrally welded together along transversely opposite side edge portions 6a, 7a of these waist region 6, 7 at a plurality of welding spots 13 arranged intermittently in a vertical direction as viewed in FIG. 1. Respective peripheral portions of the waist-hole 11 and the leg-holes 12 are provided with a waist-surrounding elastic member 16 and leg-surrounding elastic members 17, respectively, interposed between the top-and backsheets 2, 3 and bonded in a stretched state to at least one of these sheets 2, 3. The waist-surrounding elastic member 16 comprises an elastic member 16a laid on the front waist region 6 and an elastic member 16b laid on the rear waist region 7. Each of the leg-surrounding elastic members 17 comprises a front elastic member 17a laid on a part of the leg-hole's periphery extending aside toward the front waist region 6 and a rear elastic member 17b laid on a part of the same leg-hole's periphery extending aside toward the rear waist region 7 so that the respective elastic members 17a, 17b may extend from the periphery of the one leg-hole 12 across the crotch region 8 to the periphery of the other leg-hole 12.

The topsheet 2 of the diaper 1 may be formed from a nonwoven fabric or porous plastic film. The backsheet 3 may be formed from a plastic film, nonwoven fabric or composite sheet comprising these plastic film and nonwoven fabric. The core 4 may be formed from, for example, fluff pulp or a mixture of fluff pulp and super-absorbent polymer particles. In the diaper 1, the core 4 is relatively bulky and typically has a thickness in a range of 5 to 20 mm.

Figure 2:
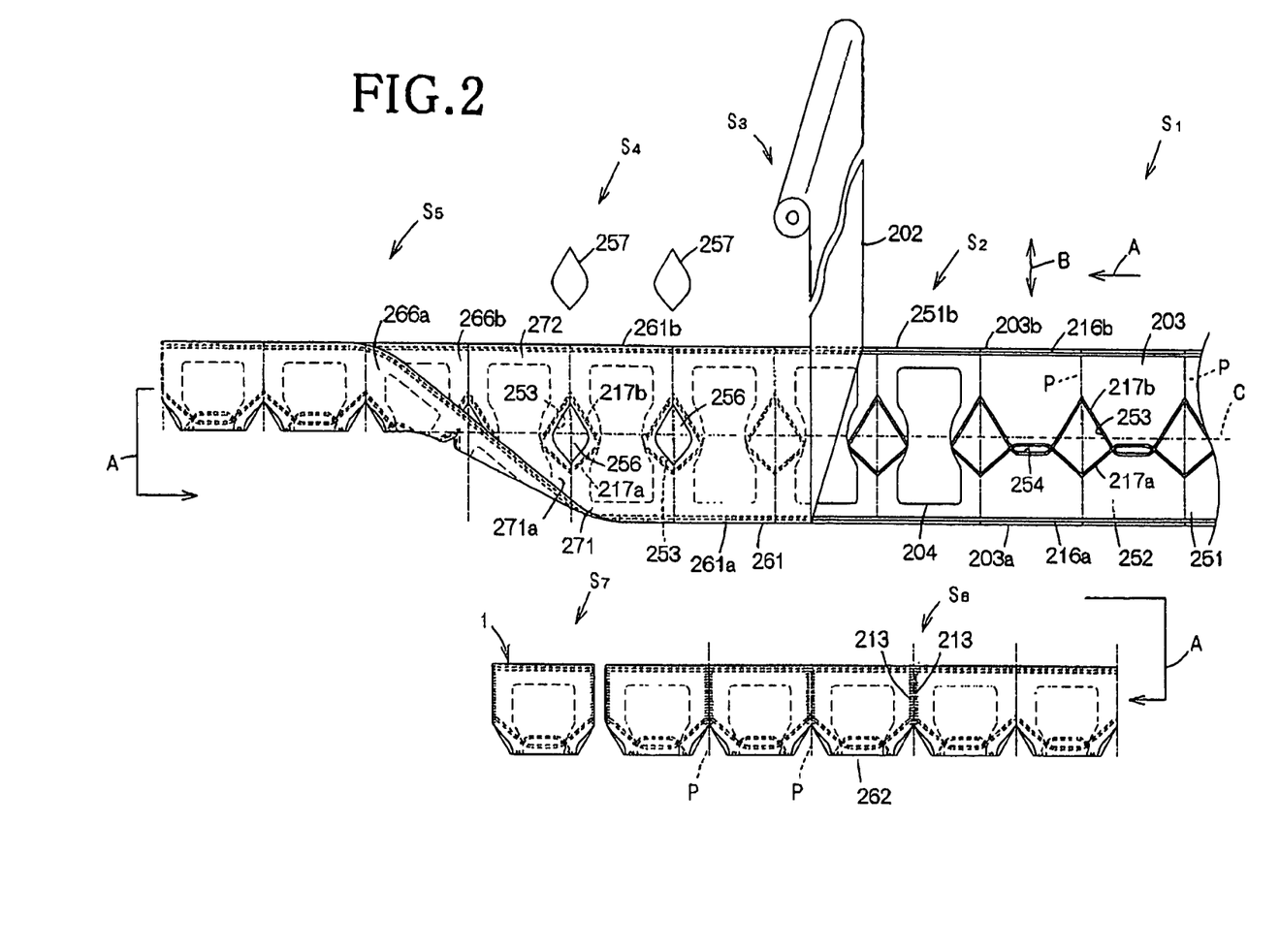
FIG. 2 is a diagram illustrating a part of a process for making the diaper.

FIG. 2 is a diagram illustrating a part of a process for making the diaper 1. In FIG. 2, an arrow A indicates the machine direction and an arrow B indicates a cross direction orthogonal to the machine direction A. On a first stage $S_1$ of this process, a liquid-impervious web 203 made of a plastic film is continuously fed from the right hand in FIG. 2. The liquid-impervious web 203 is destined to form the backsheet 3 of the diaper 1 and imaginary lines P indicate respective positions at which the liquid-impervious web 203 will be cut on the subsequent stage. A dimension between each pair of the adjacent imaginary lines P corresponds to a width of the diaper 1. The liquid-impervious web 203 has an inner surface 251, an outer surface 252 and a pair of side edge portions 203a, 203b extending in parallel to each other wherein a distance between these side edge portions 203a, 203b is bisected by a central line C. The inner surface 251 of the liquid-impervious web 203 is provided along the side edge portions 203a, 203b with first and second elastic members 216a, 216b rectilinearly extending in the machine direction A bonded in a stretched state thereto, respectively, and additionally provided, in the vicinity of the center line C, with third and fourth elastic members 217a, 217b periodically undulating in the machine direction A bonded in stretched state thereto. On each of the imaginary lines P, the third and fourth elastic members 217a, 217b are significantly spaced apart from each other in the vertical direction as viewed in FIG. 2 so as to describe a large loop 253 and, in an intermediate zone between each pair of the adjacent imaginary lines P, these elastic members 217a, 217b are slightly spaced apart from each other in the vertical direction so as to describe a small loop 254. Each pair of the adjacent large loop 253 and the small loop 254 are contiguous to each other at a cross point of the third and fourth elastic members 217a, 217b.

On a second stage $S_2$ in FIG. 2, liquid-absorbent cores 204 are placed on the inner surface 251 of the liquid-impervious web 203 so as to be intermittently arranged in the machine direction A. These cores 204 are permanently bonded to the inner surface 251 by means of hot melt adhesive (not shown) previously applied on the inner surface 251.

On a third stage $S_3$ in FIG. 2, liquid-pervious web 202 having a same width as that of the liquid-impervious web 203 is fed and bonded to the inner surface 251 of the liquid-impervious web 203 by means of hot melt adhesive (not shown). In this manner, a first composite web 261 is formed from these webs 202, 203 and the core 204. The first composite web 261 has a pair of transversely opposite side edge portions 261a, 261b each comprising transversely opposite side edge portions of the webs 202, 203.

On a fourth stage $S_4$ in FIG. 2, regions of the liquid-pervious web 202 and the liquid-impervious web 203 placed upon each other inside the respective large loops 253 defined by the third and fourth elastic members 217a, 217b are cut away from the first composite web 261 as sheet pieces 257 to form the first composite web 261 with through-holes 256.

On a fifth stage $S_5$ in FIG. 2, the first composite web 261 is folded along a center line C in two with the liquid-pervious web 202 inside. In order to obtain the aesthetically pleasing diaper 1, it is important for the first composite web 261 to be folded in two so that the transversely opposite side edge portions 261a, 261b may be substantially aligned with each other.

On a sixth stage $S_6$ in FIG. 2, respective halves of the first composite web 261 folded in two are ultrasonic- or heat-sealed along zones 213 defined on both sides of the respective imaginary lines P and thereby a second composite web 262 is obtained.

On a seventh stage $S_7$ in FIG. 2, the second composite web 262 is cut along the imaginary lines P to obtain the individual diapers 1. As will be readily understood from these stages $S_1$ through $S_7$, the liquid-pervious web 202, the liquid-impervious web 203 and the core 204 are destined to define the topsheet 2, the backsheet 3 and the core 4 of the diaper 1, respectively. Similarly, the first and second elastic members 216a, 216b are destined to define the waist-surrounding elastic members 16a, 16b of the diaper 1 and the third and fourth elastic members 217a, 217b are destined to define the leg-surrounding elastic members 17a, 17b of the diaper 1. The transversely opposite side edge portions 261a, 261b are destined to define a waist-hole's peripheral portion 61a in the front waist region 6 and a waist-hole's peripheral portion 61b in the rear waist region 7 of the diaper 1 (See FIG. 1).

Figure 3:
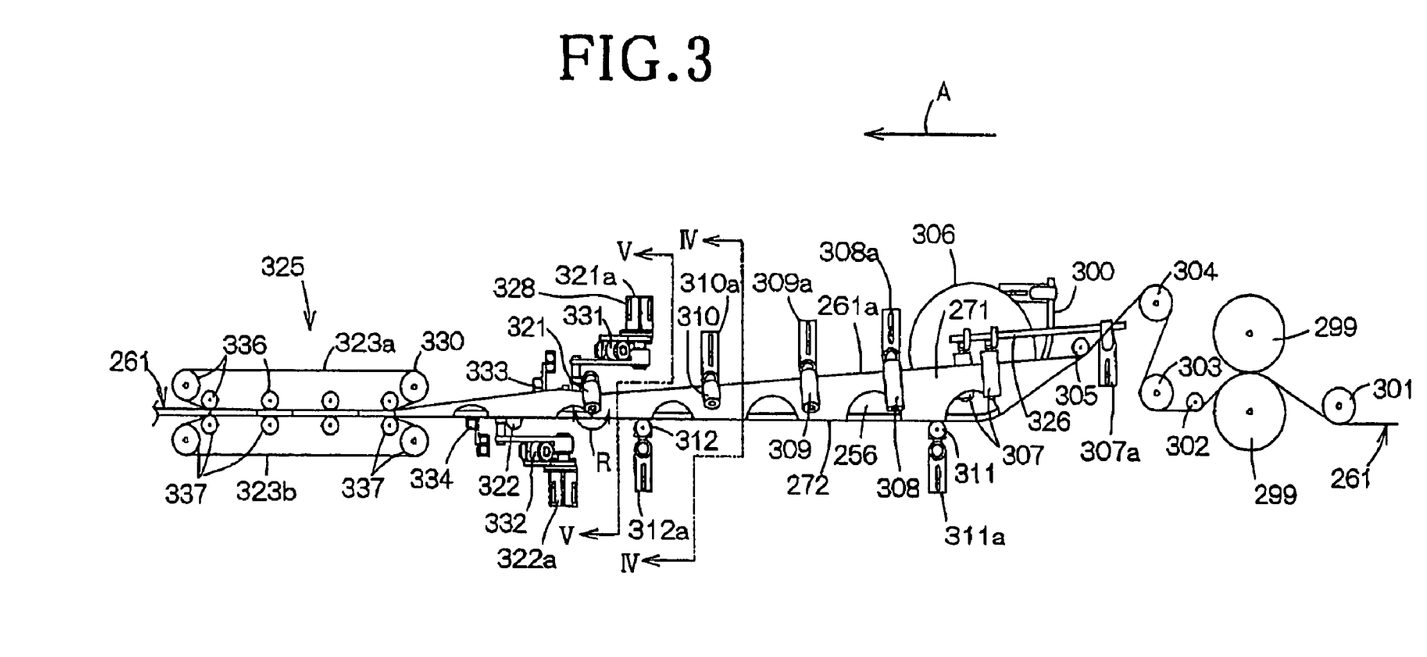
FIG. 3 is a side view illustrating an apparatus used for the part illustrated in FIG. 2.

FIG. 3 is a diagram illustrating a series of devices used to fold the first composite web 261 is folded in two to form the second composite web 262 on the fifth stage $S_5$ in FIG. 2. The first composite web 261 is fed in the machine direction A from the right hand toward the left hand as viewed in FIG. 3. After having passed first through fifth guide rolls 301, 302, 303, 304, 305 serving as a feeding means and a pair of die cut rolls 299, the first composite web 261 is guided by a sixth guide roll 306 having a large diameter and a guide bar 300 and thereby further runs in the machine direction A. The die cut rolls 299 are used to cut the sheet pieces 257 away from the first composite web 261 on the fourth stage $S_4$ in FIG. 2. The guide bar 300 extends in the machine direction A so as to come in contact with the first composite web 261 from the inner side in the vicinity of the centre line C shown in FIG. 2. The large-diameter sixth guide roll 306 has a width exceeding ½ width of the first composite web 261 and comes in contact with an upper second half region 272 of the first composite web 261 above the centre line C (See FIG. 2) from the inner side so as to maintain this second half region 272 substantially horizontal. The first composite web 261 has a lower first half region 271 below the centre line C (See FIG. 2) is guided between a pair of seventh guide rolls 307 so that the first half region 271 rises at an opening angle α (See FIG. 4) with respect to the second half region 272. Thus the first composite web 261 runs in the machine direction A as this first composite web 261 is folded along the guide bar 300. The first half region 271 is then guided in the machine direction A by eighth, ninth and tenth guide rolls 308, 309, 310 being in contact with the first half region 271 from above as viewed in FIG. 3 so that the opening angle α may be gradually reduced as the first half region 271 runs in the machine direction A. The second half region 272 is guided in the machine direction A by eleventh and twelfth guide rolls 311, 312 serving also to support the second half region 272 from underneath and thereby to maintain the second half region 272 horizontal. After the first half region 271 has come in contact with a first swing guide roll 321 and the second half region 272 has come in contact with a second swing guide roll 322, the first composite web 261 further runs toward a conveyor 325. The conveyor 325 holds the first half region 271 and the second half region 272 between a pair of upper and lower endless belts 323a, 323b to place these first and second half regions 271, 272 upon each other and conveys the first composite web 261 to the sixth stage $S_6$ in FIG. 2.

Referring to FIG. 3, the first through sixth guide rolls 301 through 306 respectively have shafts extending from a machine part mounting wall surface W (See FIG. 4) extending in the machine direction A in parallel to the plane of FIG. 3 and rotate around these shafts in the machine direction A The first composite web 261 runs in parallel to the wall surface W and the shafts of the first through sixth guide rolls 301 through 306 are orthogonal to the first half region 271 of the first composite web 261. The seventh guide rolls 307 comprise a pair of shafts extending orthogonally to the first half region 271 of the first composite web 261 and a pair of rolls rotatably mounted on the respective shafts so as to come in contact with the first half region 271 from inner and outer sides. The shafts of the respective rolls are supported by an arm 326 mounted on the wall surface W by means of brackets 307a. The guide rolls 307 rotate in the machine direction A, more exactly, in the direction in which the first half region 271 runs so that the seventh guide rolls 307 do not obstruct running of the first composite web 261 even when the first composite web 261 comes in contact with these seventh guide rolls 307. The eighth through twelfth guide rolls 308 through 312 are substantially identical one to another in construction thereof and freely rotatable. These guide rolls are position-adjustably mounted on the wall surface W by means of brackets 308a through 312a. The first and second swing guide rolls 321, 322 are position-adjustably mounted together with first and second actuators 331, 332 on the wall surface W by means of brackets 321a, 322a. A first photoelectric tube 333 is provided between the first swing guide roll 321 and an inlet of the conveyor 325 and a second photoelectric tube 334 is provided between the second swing guide roll 322 and the inlet of the conveyor 325 (See FIG. 5). The first photoelectric tube 333 and the second photoelectric tube 334 respectively are adapted to detect positions of the side edge portions 261a, 261b of the first half region 271 and the second half region 272 constituting the first composite web 261 and to supply information of the detected positions to the first actuator 331 and the second actuator 332, respectively. The conveyor 325 comprises a pair of upper and lower endless belts 323a, 323b and a plurality of upper guide rolls 336 and a plurality of lower guide rolls 337 cooperating together to guide these endless belts 323a, 323b in the machine direction A.

Figure 4:
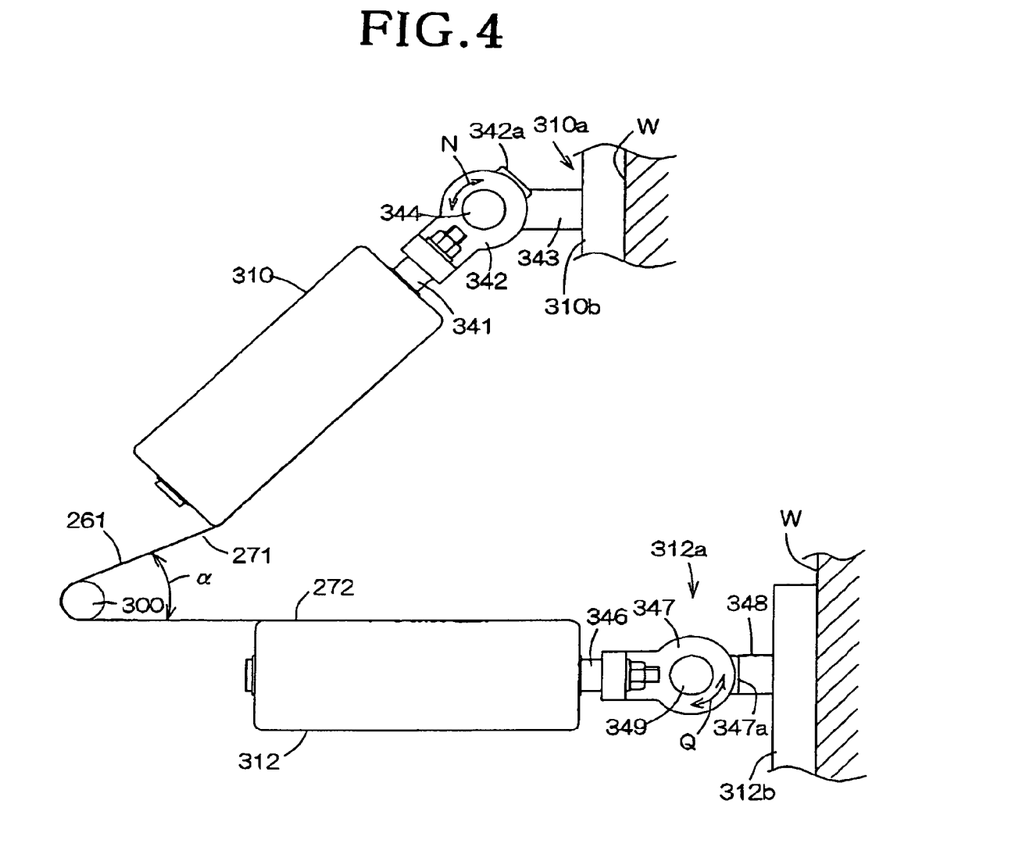
FIG. 4 is a sectional view taken along the line IV—IV in FIG. 3.

FIG. 4 is a sectional view taken along the line IV—IV in FIG. 3, showing a first composite web 261, a tenth guide roll 310 and a twelfth guide roll 312 but eliminating illustration of devices provided downstream of these two guide rolls 310, 312. In the vicinity of the center line C, the first composite web 261 is pressed against the guide bar 300 and thereby folded so as to describe a laid down V-shape. In the course of folding, the first half region 271 comes in contact with the tenth guide roll 310 from underneath as viewed in FIG. 4 while the second half region 272 comes in contact with the twelfth guide roll 312 from above as viewed in FIG. 4. In the vicinity of the guide bar 300, the first half region 271 runs at an opening angle α with respect to the second half region 272 which is practically horizontal. The tenth guide roll 310 is freely rotatable around the shaft 341 which is fixed to a first elbow 342 of a composite elbow joint 310a consisting of the first elbow 342 and a second elbow 343. The first elbow 342 is mounted on the shaft 344 of the second elbow 343 so that the first elbow 342 may be slidable in a circumferential direction N of the shaft 344 and the first elbow 342 may be fixed to the shaft 344 by a bolt 342a. The position of the composite elbow joint 310a having the first and second elbows 342, 343 can be position-adjustable in vertical direction along the wall surface W which extends vertically as viewed in FIG. 4. The composite elbow joint 310a allows the tenth guide roll 310 to be tilted in the vertical direction at a desired angle with respect to the wall surface W. It is also possible to construct the composite elbow joint 310a so that the tenth guide roll 310 can be tilted in the machine direction A at a desired angle with respect to the wall surface W. The tenth guide roll 310 which is position- as well as angle-adjustable in this manner crosses the first half region 271 at an opening angle of 90° or less as measured in the direction in which the first half region 271 runs. The twelfth guide roll 312 is freely rotatable around the shaft 346 which is fixed to a first elbow 347 of a composite elbow joint 312a. The first elbow 347 is mounted on a shaft 349 of a second elbow 348 so that the first elbow 347 may be slidable in a circumferential direction Q of the shaft 349 and the first elbow 342 may be fixed to the shaft 349 by a bolt 347a. In the case of the composite elbow joint 312a consisting of these first and second elbows 347, 348, a platy base 312b integral with the second elbow 348 is position-adjustable in vertical direction along the wall surface W. It is also possible to construct the composite elbow joint 312a so that the twelfth guide roll 312 can be tilted in the machine direction A at a desired angle with respect to the wall surface W. The twelfth guide roll 312 which is position- as well as angle-adjustable in this manner crosses the second half region 272 at an angle of 90° or less as measured in the direction in which the second half region 272 runs. The first composite web 261 is under a tension in the machine direction A and the tenth and twelfth guide rolls 310, 312 are pressed against this first composite web 261 so that the desired opening angle α or the angle or an angle close to α may be maintained; the tension of the first composite web 261 in the machine direction A may be maintained; and the transversely opposite side edge portions 261a, 261b of the first composite web 261 may be prevented from moving inward in the transverse direction under such tension. The eighth and ninth guide rolls 308, 309 shown in FIG. 3 are mounted on the wall surface W as in the case of the tenth guide roll 310. Vertical positions of these guide rolls 308, 309 on the wall surface W as well as angles included between the respective guide rolls 308, 309 and the wall surface W can be adjusted so that the opening angle α may be gradually reduced and the first half region 271 may correspondingly get nearer to the second half region 272. While the eleventh guide roll 311 shown in FIG. 3 is similar to the twelfth guide roll 312 in that the eleventh guide roll 311 is mounted on the wall surface W, a vertical position of this guide roll 311 as well as an angle between this guide roll 311 and the wall surface W can be appropriately adjusted if it is required to guide the first composite web 261.

Figure 5:
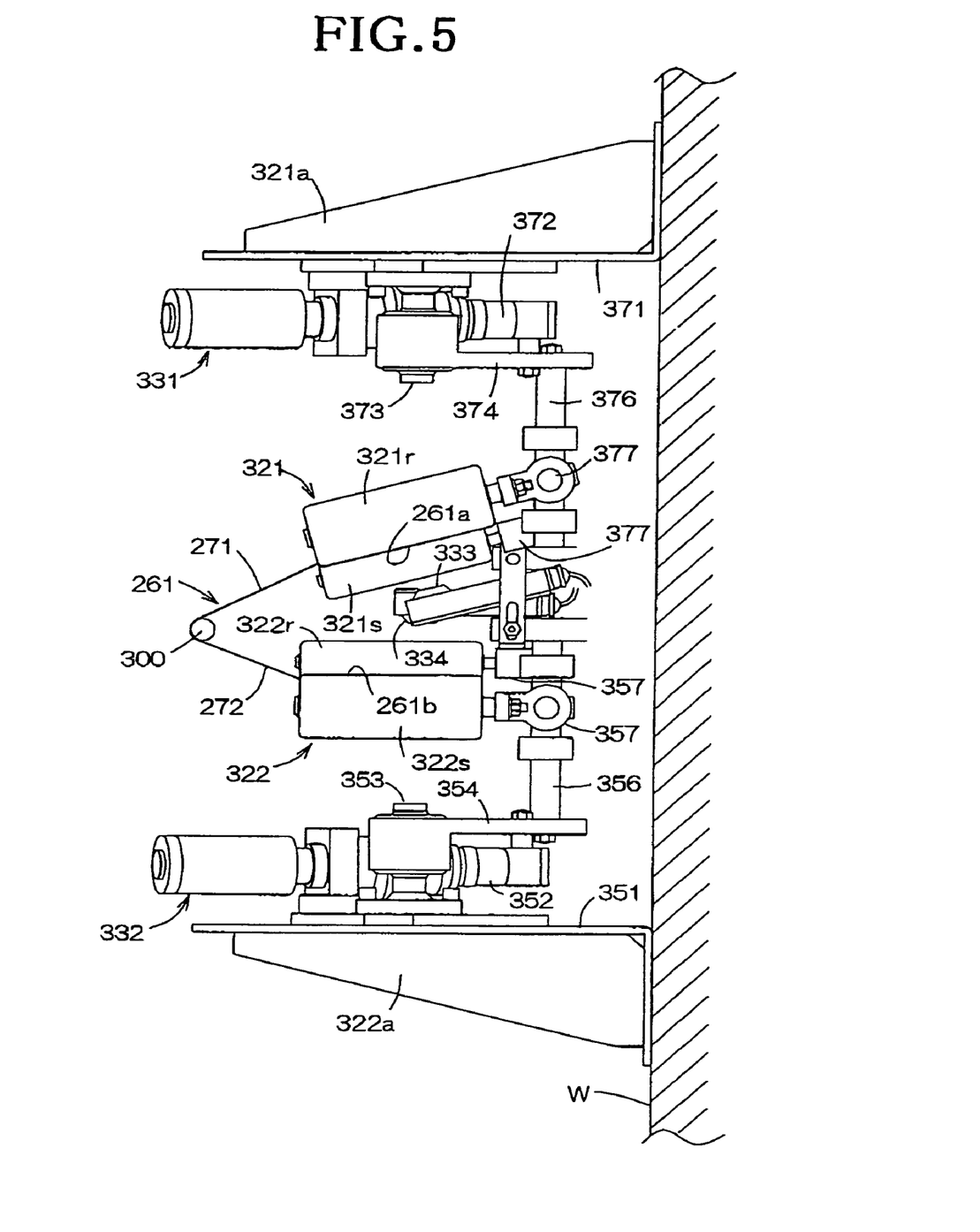
FIG. 5 is a sectional view taken along the line V—V in FIG. 3.

FIG. 5 is a sectional view taken along the line V—V in FIG. 3, showing the first composite web 261, a first swing guide roll 321 and a second swing guide roll 322 but eliminating illustration of a conveyor 325 provided downstream thereof. At an upper level on the wall surface W, a first actuator 331 is mounted on a horizontally overhanging portion 371 of a bracket 321a. The first actuator 331 comprises a first retractable arm 372 which is retractable in the plane extending in parallel to the horizontally overhanging portion 371, a first swing arm 374 driven by the first retractable arm 372 to swing around a first vertical shaft 373 and a first supporting bar 376 vertically extending downward from the first swing arm 374. A pair of first swing guide rolls 321 are mounted on the first supporting bar 376 by means of composite elbow joints 377, respectively, so that the respective first swing guide rolls 321 may be angle-adjustable with respect to the first supporting bar 376. Such pair of first swing guide rolls 321 are adapted to be held in contact with the respective side edge portions 261a of the first composite web 261 in its first half region 271 and comprise an upper guide roll 321r adapted to come in contact with the outer surface of the first composite web 261 in its first half region 271 from above as viewed in FIG. 5 and a lower guide roll 321s adapted to come in contact with the inner surface of the first half region 271 from underneath as viewed in FIG. 5. A first photoelectric tube 333 is located downstream of the first swing guide rolls 321 in the machine direction A.

As will be seen below the first swing guide rolls 321 in FIG. 5, a second actuator 332 is mounted on a horizontally overhanging portion 351 of a bracket 322a extending from the wall surface W. The second actuator 332 comprises a second retractable arm 352 which is retractable in the plane extending in parallel to the horizontally overhanging portion 351, a second swing arm 354 driven by the second retractable arm 352 to swing around a second vertical shaft 353 and a second supporting bar 356 vertically extending upward from the second swing arm 354. A pair of second swing guide rolls 322 are mounted on the second supporting bar 356 by means of composite elbow joints 357, respectively, so that the respective second swing guide rolls 322 may be angle-adjustable with respect to the second supporting bar 356. Such pair of second swing guide rolls 322 are adapted to be held in contact with the respective side edge portions 261b of the first composite web 261 in its second half region 272 and comprise a lower guide roll 322s adapted to come in contact with the outer surface of the first composite web 261 in its second half region 272 from underneath as viewed in FIG. 5 and an upper guide roll 322r adapted to come in contact with the inner surface of the second half region 272 from above as viewed in FIG. 5. A second photoelectric tube 334 is located downstream of the second swing guide rolls 322 in the machine direction A.

The first and second swing guide rolls 321, 322 shown in FIGS. 3 and 5 operate as follows. The first photoelectric tube 333 and the second photoelectric tube 334 shown in FIG. 5 are adapted to position-detect the transversely opposite side edge portions 261a of the first composite web 261 in the first half region 271 and the transversely opposite side edge portions 261b of the first composite web 261 in the second half region 272 and then to supply the first and second actuators 331, 332 with the relevant position data. The first and second actuators 331, 332 are adapted to compare the respective position data supplied thereto to the position data predetermined for the side edge portions 261a and the side edge portions 261b, respectively, and, depending on a difference of positions, to extend or retract the first and second retractable arms 372, 352 so that the actual positions may get near to the predetermined positions. The first swing arm 374 and the first supporting bar 376 swing around the first vertical shaft 373 as the first retractable arm 372 is extended or retracted. Swing of the first supporting bar 376 causes the first swing guide rolls 321 mounted on this bar 376 to swing in a direction indicated by a double-headed arrow R in FIG. 3 so that a crossing angle of the first swing guide rolls 321 with respect to the machine direction A. In consequence, the side edge portions 261a against which these first swing guide rolls 321 are pressed may be moved outward or inward in the transverse direction of the first composite web 261 toward the predetermined positions of these side edge portions 261a. Similarly, the second swing arm 354 and the second supporting bar 356 swing around the second vertical shaft 353 as the second retractable arm 352 is extended or retracted. Swing of the second supporting bar 356 causes the second swing guide rolls 322 mounted on this bar 356 to swing in the same manner as the first swing guide rolls 321 so that a crossing angle of the second swing guide rolls 322 with respect to the machine direction A. In consequence, the side edge portions 261b against which these second swing guide rolls 322 are pressed may be moved outward or inward in the transverse direction of the first composite web 261 toward the predetermined positions of these side edge portions 261b. It should be understood here that movement of the side edge portions 261a, 261b in the transverse direction of the first composite web 261 includes two difference cases. In one case, these side edge portions 261a, 261b merely be moved in the cross direction B. In the other case, these side edge portions 261a, 261b are elastically stretched or contracted in the cross direction B.

The first and second actuators 331, 332 operating in the manner as has been described contain the previously input data relating to the predetermined positions of the side edge portions 261a, 261b when the first composite web 261 is folded in two and these transversely opposite side edge portions 261a, 261b are placed one upon another in alignment. These actuators 331, 332 allow the first composite web 261 folded in two with the respective side edge portions 261a, 261b being substantially in alignment to go into the conveyor 325. The first swing guide rolls 321 and the second swing guide rolls 322 respectively comprise the pair of guide rolls 321r, 321s; 322r, 322s both adapted to be pressed against both surfaces of the first composite web 261. Swing of these pairs of guide rolls around the first supporting bar 376 and the second supporting bar 356, respectively, causes the side edge portions 261a, 261b of the first composite web 261 to be reliably and rapidly moved in the cross direction B. It should be noted here that, if the first and second swing guide rolls 321, 322 have a high frictional coefficient with respect to the first composite web 261, it will be possible to eliminate one of the pair of guide rolls 321r, 321s and one of the pair of guide rolls 322r, 322s. Regarding the seventh through twelfth guide rolls 307 through 312 located upstream of the first and second swing guide rolls 321, 322, the number of the guide rolls may be appropriately increased or decreased and a distance between each pair of the adjacent guide rolls may be appropriately adjusted.

Along the stages illustrated in FIG. 3, the seventh through the twelfth guide rolls 307 through 312 are pressed against the side edge portions 261a, 261b of the first and second half regions 271, 272 at a crossing angle of 90° or less so that the opening angle α between the first and second half regions 271, 272 may be gradually reduced. In addition, immediately before the conveyor 325, the first swing guide rolls 321 are adapted to act upon the side edge portions 261a and the second swing guide rolls 322 are adapted to act upon the side edge portions 261b so that the side edge portions 261a and the side edge portions 261b may be independently position-adjusted so as to get nearer to the predetermined positions. The method and the apparatus according to this invention used for position-adjustment of the side edge portions 261a, 261b facilitate the respective side edge portions 261a, 261b to be moved to the predetermined positions whether the liquid-pervious web 202 and/or the liquid-impervious web 203 is (are) elastically stretchable or inelastically stretchable. As used herein, the predetermined positions are not limited to the positions at which the side edge portions 261a as well as the side edge portions 261b are placed one upon another but also refer to the positions at which the side edge portions 261a and the side edge portions 261b are respectively out of alignment by desired dimensions.

While this invention has been exemplarily described above on the basis of the stages on which the web as stock material for disposable pants-type diaper 1 is folded in two, this invention is applicable also to the case in which flexible sheet material continuously running in the machine direction such as nonwoven fabric, woven fabric, paper or plastic film is folded in two with the transversely opposite side edge portions of this web placed upon each other in mutual alignment or spaced from each other by a desired dimension.

This invention is primarily characterized in that the web continuously fed in the machine direction is folded in two in the cross direction by pressing the guide rolls against the respective side edge portions of the web so that the opening angle of the web folded in two may be gradually reduced and, immediately before the web is completely folded in two, the respective side edge portions may be moved toward the predetermined positions by the first and second swing guide rolls adapted to operate independently of each other. In this way, the respective side edge portions can be moved toward the predetermined positions whether the web is elastically stretchable or inelastically stretchable. Even the web having bulky cores arranged intermittently in the longitudinal direction can be easily folded in two so that the side edge portions thereof may coincide with the predetermined positions.

This invention allows the pants-type wearing article such as disposable pants-type diaper to be finished to have the aesthetically improved peripheral portion of the waist-hole.

What is claimed is:

1. An apparatus for continuously folding a web continuously fed in a machine direction in two along a folding guide line extending in parallel to said machine direction in a cross direction orthogonal to said machine direction, said apparatus comprising:

a first means located upstream in said machine direction and adapted to feed said web unfolded in said transverse direction;

a second means located downstream in said machine direction and adapted to convey said web having been folded in two;

a guide means interposed between said first means and said second means and adapted to be pressed against said web along said folding guide line to fold said web in two;

a plurality of guide rolls arranged intermittently in said machine direction and adapted to be held in contact with said side edge portions, each of said guide rolls having a rotary shaft crossing the side edge portions of said web at an angle of 90° or less opening in the transverse direction of said web;

swing guide rolls located downstream of said guide rolls and adapted to be held in contact with said side edge portions of said web and, in addition, to swing so that a crossing angle thereof with respect to said side edge portions of said web may be changed;

a detector means located downstream of said swing guide rolls and adapted to detect positions of said side edge portions in said cross direction; and actuators causing said swing guide rolls to swing on the basis of differences between data supplied from said detector means representing actual positions of said side edge portions and data representing expected positions of said side edge portions to move said side edge portions toward said expected positions.

* * * * *